United States Patent
Henningsen et al.

(10) Patent No.: US 6,207,864 B1
(45) Date of Patent: Mar. 27, 2001

(54) PROCESS FOR PREPARING CYCLOPROPYLACETYLENE

(75) Inventors: Michael Henningsen, Frankenthal; Armin Stamm, Mainz; Martin Fischer, Ludwigshafen; Wolfgang Siegel, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/380,382

(22) PCT Filed: Feb. 18, 1998

(86) PCT No.: PCT/EP98/00927

§ 371 Date: Sep. 1, 1999

§ 102(e) Date: Sep. 1, 1999

(87) PCT Pub. No.: WO98/40333

PCT Pub. Date: Sep. 17, 1998

(30) Foreign Application Priority Data

Mar. 7, 1997 (DE) ................................ 197 09 401
Jul. 26, 1997 (DE) ................................ 197 32 292

(51) Int. Cl.[7] .............. C07C 45/30; C07C 49/293; C07C 2/02; C07C 11/00
(52) U.S. Cl. .......................... 568/348; 568/343; 568/364; 585/359; 585/534; 585/538
(58) Field of Search ................................ 585/359, 534, 585/538; 568/348, 343, 364

(56) References Cited

U.S. PATENT DOCUMENTS

| 3,715,407 | 2/1973 | Relles ................................ 260/668 |
| 4,044,060 | 8/1977 | Buysch et al. ..................... 260/651 |

FOREIGN PATENT DOCUMENTS

| 1192205 | 12/1962 | (DE) . |
| 251 246 | 1/1988 | (EP) . |
| 578293 | 2/1972 | (SU) . |
| 555079 | 1/1976 | (SU) . |
| 572445 | 4/1976 | (SU) . |
| 96/22955 | 8/1996 | (WO) . |

OTHER PUBLICATIONS

Hudson et al., *J. of Am. Chem. Soc.*, 94(4), 1972, 1158–1163.
*Synthesis*, 1972, p. 703.

*Primary Examiner*—Sreeni Padmanabhan
(74) *Attorney, Agent, or Firm*—Keil & Weinkauf

(57) ABSTRACT

The invention relates to a process for the halogenation of cyclopropylmethyl ketone with at least one dihalo-triorganophosphorane of the general formula I $$R_3PHal_2 \qquad (I),$$

in which the radicals R can be the same or different and denote a saturated or unsaturated aliphatic $C_1$–$C_{20}$ hydrocarbon radical, a phenyl or ($C_1$–$C_4$ alkyl)phenyl radical, which may be optionally substituted by one or two fluorine, chlorine and/or nitro groups, P stands for phosphorus and Hal denotes chlorine, bromine, or iodine, at a temperature of from 800° to 130° C., where the dihalo-triorganophosphane of the general formula (I) is synthesized in situ from triorganophosphane oxide or triorganophosphane sulfide of the general formula II $$R_3PA \qquad (II),$$

in which R is as defined above with respect to formula I and A denotes oxygen or sulfur, using a halogenating agent, wherein the triorganophosphane oxide or triorganophosphane sulfide is used in catalytic amounts, to the halogenation product of cyclopropylmethyl ketone obtained in said process, and to a process for the conversion of said halogenation product to cyclopropylacetytene.

6 Claims, No Drawings

PROCESS FOR PREPARING CYCLOPROPYLACETYLENE

This is the U.S. National Stage Application of PCT/EP98/00927 filed Feb. 18, 1998.

The present invention relates to an improved process for the halogenation of cyclopropylmethyl ketone using dihalo-triorganophosphoranes, to the halogenation products obtained in said process, and to a process for the preparation of cyclopropylacetylene by dehydrohalogenation of said halogenation products.

Cyclopropylacetylene is disclosed by PCT/WO 96/22955 as an intermediate for an inhibitor of the HIV reserve transkriptase. The Human Immuno Deficiency Virus is the cause of the Acquired Immune Deficiency Syndrome (AIDS). The viral HIV reserve transkriptase is a key enzyme for replication of the HI Deficiency Virus in the host organism.

Since the key enzyme is inhibited by inhibitors of which cyclopropylacetylene is an intermediate, cyclopropylacetylene is of great significance in the preparation of medicaments to combat AIDS.

PCT/WO 96/22955 discloses a process for the preparation of cyclopropylacetylene by cyclization of 5-halo-1-pentyne using strong bases such as butyllithium in an aprotic solvent followed by quenching of the resulting lithium salt with a proton source such as ammonium chloride.

J. Amer. Chem. Soc. 94, 1158 (1972) describes a process for the preparation of cyclopropylacetylene, in which cyclopropylmethyl ketone is chlorinated with phosphorus pentachloride and the 1,1-dichloro-1-cyclopropylethane isolated from the chlorination product is then dehydrochlorinated with sodium amide in liquid ammonia to form cyclopropylacetylene.

Synthesis 1972, 703 reveals that the chlorination of cyclopropylmethyl ketone with phosphorus pentachloride only takes place without appreciable opening of the cyclopropane ring if carried out using purified, acid-free phosphorus pentachloride.

In order to prevent opening of the cyclopropane ring during chlorination, the processes described in SU 555,079, SU 578,293, and SU 572,445 effect chlorination in the presence of an organic base such as pyridine or N,N-diethylaniline.

The aforementioned chlorinations of cyclopropylmethyl ketone with phosphorus pentachloride suffer from the drawback that the phosphorus pentachloride, which is extremely sensitive to hydrolysis, can only be handled in absolute absence of moisture and must be used in equimolar amounts. Furthermore, said chlorinations produce phosphorus oxychloride, which must be removed by hydrolysis, since it can be removed from the chlorination product by distillation either not at all or only with great difficulty.

U.S. Pat. No. 3,715,407 discloses a process for the chlorination of ketones using molar excesses, based on the ketone, of dichloro-triorganophosphorane prepared in situ from triorganophosphane oxide and phosgene. This process suffers from the drawback that the triorganophosphane oxide must be used in large excess over the ketone. Owing to the poor solubility of triorganophosphane oxide, large quantities of solvent are necessary to carry out the reaction, and continuous operation of the process involves considerable technical problems.

It is an object of the invention, therefore, to overcome the above drawbacks.

Accordingly, we have found a novel and improved process for the halogenation of cyclopropylmethyl ketone with at least one dihalo-triorganophosphorane of the general formula I $$R_3PHal_2 \quad (I),$$

in which the radicals R can be the same or different and denote a saturated or unsaturated aliphatic $C_1$–$C_{20}$ hydrocarbon radical, a phenyl or ($C_1$–$C_4$ alkyl)phenyl radical, which may be optionally substituted by one or two fluorine, chlorine and/or nitro groups, preferably in ortho and/or para position relative to the phosphorus atom, 4-chloro-, 4-fluoro-, or 4-nitro-substituted phenyl radicals being particularly preferred, P stands for phosphorus and Hal denotes chlorine, bromine, or iodine, at a temperature of from 80° to 130° C., where the dihalo-triorganophosphorane of the general formula (I) is synthesized in situ from triorganophosphane oxide or triorganophosphane sulfide of the general formula II $$R_3PA \quad (II),$$

in which R is as defined above with respect to formula I and A denotes oxygen or sulfur, using a halogenating agent, wherein the triorganophosphane oxide or triorganophosphane sulfide is used in catalytic amounts.

In the process of the invention dichloro-triorganophosphoranes of the general formula I are preferably synthesized in situ, particular preference being given to dichlorotriphenylphosphorane, a dichloro-tri($C_6$–$C_8$ alkyl)phosphorane, dichloro-tri(4-chlorophenyl)phosphorane, dichloro-tri(4-fluorophenyl)phosphorane, dichloro-tri(4-nitrophenyl)phosphorane, or mixtures thereof.

Suitable halogenating agents for use in the process of the invention are known per se and are described, for example, in Houben-weyl, Methoden der organischen Chemie, Vol. E2, 872 (1982). We prefer to use a chlorinating agent in the process of the invention, examples of which are chlorine, oxalyl chloride, thionyl chloride, phosgene, diphosgene or triphosgene, of which phosgene is preferred.

The halogenation of the cyclopropylmethyl ketone is preferably carried out at a temperature of from 90° to 120° C., more preferably from 90° to 100° C., and under a pressure of from 0.8 to 1.5 bar, preferably under standard pressure, the halogenating agent being used in a molar ratio of from 0.5:1 to 2:1 and preferably from 0.5:1 to 1.0:1 and the triorganophosphane oxide or triorganophosphane sulfide is used in equimolar amounts, preferably catalytic amounts ranging from 0.5 to 5 mol % and more preferably from 1.0 to 2.5 mol %, based, in each case, on the cyclopropylmethyl ketone.

A particularly recommendable routine for carrying out the halogenation is to place the halogenating agent in the reactor and then add a solution of triorganophosphane oxide or triorganophosphane sulfide in cyclopropylmethyl ketone. Alternatively, only a portion of the total amount of halogenating agent is initially placed in the reactor, the remainder thereof being added after the solution of triorganophosphane oxide or triorganophosphane sulfide in cyclopropylmethyl ketone has been added. This routine is particularly recommended when phosgene is used as halogenating agent.

Another possibility is to place from 5 to 25 wt %, preferably from 15 to 25 wt %, of the total amount of triorganophosphane oxide or triorganophosphane sulfide in cyclopropylmethyl ketone in the reactor, to add the chlorinating agent, and then to add the remainder of the solution. It is of course possible, if desired, to place all of the solution of triorganophosphane oxide or triorganophosphane sulfide in cyclopropylmethyl ketone in the reactor as initial batch.

The process of the invention may be carried out batchwise or continuously, preference being given to continuous operation for economical reasons.

Triorganophosphane oxides can be prepared, for example, by the method described in Houben-Weyl, Methoden der organischen Chemie, Vol. E2 (1982), page 2.

A mixture of tri($C_6$–$C_8$ alkyl)phosphane oxides is marketed, for example, by Cytec Industries Inc., N.J., USA under the Trade Name Cyanex[a] 923.

Triorganophosphane sulfides can be prepared, for example, by the process described in Houben-weyl, Methoden der organischen Chemie, Vol. E2 (1982), page 79.

The process of the invention for the halogenation of cyclopropylmethyl ketone is preferably carried out in the absence of solvent. However, the process of the invention may, if desired, be carried out in an inert solvent having a boiling point preferably above 110° C. and in which the dihalo-triorganophosphorane is soluble.

Suitable solvents are, for example, halogenated aromatic hydrocarbons such as chlorobenzene, 1-methylnaphthalene, xylene, or mesitylene, of which xylene and mesitylene are preferred.

By-products formed in the process of the invention for the halogenation of cyclopropylmethyl ketone are triorganophosphane oxides or triorganophosphane sulfides of formula II, from which the halogenation product can be separated by distillation.

The process of the invention for halogenation of cyclopropylmethyl ketone has the advantage that both the catalytic amounts of triorganophosphane oxide or triorganophosphane sulfide used and the reaction products are completely soluble in the reaction mixture, by reason of which the formation of deposits on parts of the plant, especially choking of valves, is avoided. Considered economically, the process of the invention may well be carried out continuously in the absence of solvent.

Thus the present application also relates to the halogenation product of cyclopropylmethyl ketone which is produced by the process of the invention, particularly after separation thereof, by distillation, from the resultant triorganophosphane oxides or triorganophosphane sulfides.

We have also found a process for the preparation of cyclopropylacetylene, wherein a halogenation product produced by the process of the invention for the halogenation of cyclopropylmethyl ketone is treated with a strong base at a temperature of from –33° to 250° C., preferably from 80° to 140° C. and more preferably from 80° to 120° C.

Examples of suitable strong bases for the preparation of cyclopropylacetylene are sodium amide, alkali metal alkoxides such as sodium ethoxide, potassium ethoxide, sodium methoxide, potassium methoxide, potassium tert-butylate, sodium hydroxide and potassium hydroxide, and alkali metal salts of glycol ethers such as potassium butyltriglycolate, of which potassium hydroxide is preferred. The strong base is used in the process of the invention in a suitable solvent, for example sodum amide in ammonia, sodium ethoxide or potassium ethoxide in ethanol, potassium tert-butylate in dimethyl sulfoxide, and potassium hydroxide or potassium methoxide in glycol ethers such as triethylene glycol dimethyl ether, ethoxyethanol, methyl triglycol, butyl triglycol, the use of potassium hydroxide, potassium methoxide or sodium methoxide in glycol ethers being preferred, while the use of potassium methoxide in glycol ethers is particularly preferred.

In addition to the solvent in which the strong base is used, the reaction mixture used in the process of the invention for the preparation of cyclopropylacetylene may contain a further inert solvent having a boiling point below 170° C., for example toluene.

The ratio, by weight, of the strong base to the halogenation product of the cyclopropylmethyl ketone is from 10:1 to 0.5:1.

The invention is illustrated below with reference to the following examples.

EXAMPLES

Chlorination of cyclopropylmethyl ketone

Example 1

7 g of triphenylphosphane oxide were dissolved in 42 g of xylene, and phosgene was passed in at a temperature of from 100° to 110° C. until phosgene reflux was established in the condenser. Over a period of 1 h, 42 g of cyclopropylmethyl ketone were added dropwise while the introduction of phosgene (to a total of 66 g) was continued. On completion of the addition, the batch was allowed to react for a further hour at 110° C., after which superfluous phosgene was purged out with nitrogen.

A yield of 8 g of 1-cyclopropylvinyl chloride and 26.3 g of 1-cyclopropyl-1,1-dichloroethane was obtained, as determined by gas chromatography.

Example 2

14 g of triphenylphosphane oxide were dissolved in 42 g of xylene, and phosgene was passed in at a temperature of from 100° to 110° C. until phosgene reflux was established in the condenser. Over a period of 1 h, 42 g of cyclopropylmethyl ketone were added dropwise while the introduction of phosgene (to a total of 66 g) was continued. On completion of the addition, the batch was allowed to react for a further hour at 110° C., after which superfluous phosgene was purged out with nitrogen. A yield of 8.7 g of 1-cyclopropylvinyl chloride and 1.74 g of 1-cyclopropyl-1,1-dichloroethane was obtained, as determined by gas chromatography.

Example 3

7 g of triphenylphosphane oxide were dissolved in 42 g of methylnaphthalene, and phosgene was passed in at a temperature of from 100° to 110° C. until phosgene reflux was established in the condenser. Over a period of 1 h, 42 g of cyclopropylmethyl ketone were added dropwise while the introduction of phosgene (to a total of 54 g) was continued. On completion of the addition, the batch was allowed to react for a further hour at 110° C., after which superfluous phosgene was purged out with nitrogen.

A yield of 9.5 g of 1-cyclopropylvinyl chloride and 3.5 g of 1-cyclopropyl-1,1-dichloroethane was obtained, as determined by gas chromatography.

Example 4

3.5 g of triphenylphosphane oxide were dissolved in 42 g of methylnaphthalene, and phosgene was passed in at a temperature of from 100° to 110° C. until phosgene reflux was established in the condenser. Over a period of 1 h, 42 g of cyclopropylmethyl ketone were added dropwise while the introduction of phosgene (to a total of 54 g) was continued. On completion of the addition, the batch was allowed to react for a further hour at 110° C., after which superfluous phosgene was purged out with nitrogen. A yield of 11.3 g of 1-cyclopropylvinyl chloride and 12.3 g of 1-cyclopropyl-1,1-dichloroethane was obtained, as determined by gas chromatography.

Example 5

7 g of triphenylphosphane oxide were dissolved in 84 g of cyclopropylmethyl ketone. Phosgene was passed in at a temperature of 110° C. over a period of 2.5 h until phosgene reflux was established in the condenser. Following a further reaction period of 1 h at 110° C., superfluous phosgene was purged out with nitrogen. A yield of 19.3 g of 1-cyclopropylvinyl chloride and 12.65 g of 1-cyclopropyl-1,1-dichloroethene was obtained, as determined by gas chromatography.

Example 6

Phosgene was passed into a glass flask at 100° C. until a strong reflux was established. 13.9 g of triphenylphosphane oxide were dissolved in 168 g of cyclopropylmethyl ketone at room temperature, and the solution was fed dropwise to the phosgene. More phosgene was introduced over a period of 9 h. The total amount of phosgene used was 220 g. On completion of the introduction of phosgene, the reaction was allowed to continue for a further 2 h at 100° C., after which excess phosgene was purged out with nitrogen. Distillation carried out at an overhead temperature of from 94° to 95° C. and a pressure of 1013 mbar yielded a halogenation product comprising 80 g of cyclopropylvinyl chloride and 44.5 g of dichlorocyclopropylethane, as determined by gas chromatography.

Example 7

28 g of triphenylphosphane oxide were dissolved in 336 g of cyclopropylmethyl ketone. 89 g of phosgene were passed into 73 g of this solution over a period of 2 h at a temperature of 105° C. until reflux was established. Then, over a period of 12.5 h at 90°–100° C., 291 g of the solution of triphenylphosphane oxide in cyclopropylmethyl ketone were added and 350 g of phosgene were introduced. A further 25 g of phosgene were then introduced at 95° C. On completion of the introduction of phosgene, excess phosgene was purged out with nitrogen. The crude product (522 g) thus obtained contained 160 g of cyclopropylvinyl chloride and 183 g of dichlorocyclopropylethane, as determined by gas chromatography.

Example 8

7 g of triphenylphosphane oxide were dissolved in 84 g of cyclopropylmethyl ketone. 10 mL (10 vol %) of this solution were placed in a stirred vessel provided with two condensers and diphosgene was introduced at room temperature until reflux was established, during which operation the temperature rose to 63° C. The remaining 90 mL of the solution of triphenylphosphane oxide in cyclopropylmethyl ketone were then added at 90°–95° C., and 126 g of diphosgene were introduced over a period of 9 h. On completion of the introduction of diphosgene, the reaction was allowed to continue for 2 h at 90°–95° C., after which excess diphosgene was purged out with nitrogen. The crude product thus obtained contained 21.3 g of cyclopropylvinyl chloride and 34.4 g of dichlorocyclopropylethane, as determined by gas chromatography.

Example 9

10 g of phosgene were condensed into continuous reaction apparatus. A solution of 2.5 mol % of triphenylphosphane oxide in cyclopropylmethyl ketone was then metered in continuously at such a rate that the feed of cyclopropylmethyl ketone was from 0.25 to 0.3 mol/h.

In all, 1713.5 g of cyclopropylmethyl ketone and 1948 g of phosgene were caused to react over a total period of 81 hours. The effluent was found to contain, as determined by gas chromatography, 20 wt % of 1,1-dichlorocyclopropylethane (476 g) and 31 wt % of cyclopropylvinyl chloride (732 g), equivalent to a space-time yield of 0.13 mol of desired product per hour.

Synthesis of cyclopropylacetylene

Example 10

A solution of 21 g of 1-cyclopropylvinyl chloride and 4.9 g of 1-cyclopropyl-1,1-dichloroethane in 13 g of toluene was fed dropwise at a rate of 8 mL/h to a mixture of 20 g of KOH in 120 g of butyl triglycol heated at 170° C.

The resulting low boilers were continuously distilled from the reaction mixture and condensed in a cooled receiver filled with 16 g of toluene.

The two-phase distillate consisted of 6.2 g of water and 47.6 g of organic phase containing 30.5 wt % of cyclopropylacetylene and 3.1 wt % of 1-cyclopropylvinyl chloride. This is equivalent to a conversion of 94% and a selectivity toward cyclopropyacetylene of 84%.

Example 11

A solution of 133 g of 1-cyclopropylvinyl chloride and 90.3 g of 1-cyclopropyl-1,1-dichloroethane in 50 g of methanol was fed dropwise at a rate of 40 mL/h to a mixture of 179.3 g of 95 wt % strength potassium methoxide in 800 g of butyl triglycol heated at 110° C.

The resulting low boilers were continuously distilled from the reaction mixture and condensed in a cooled receiver filled with 150 g of methanol.

The resulting distillate consisted of 100.7 g of cyclopropylacetylene, 13.8 g of 1-cyclopropylvinyl chloride and 261 g of methanol. This is equivalent to a conversion of 93% and a selectivity toward cyclopropyacetylene of 84%. By distillation followed by extraction with water it was possible to purify the cyclopropylacetylene to a content of 99.5%.

What is claimed is:

1. A process for the halogenation of cyclopropylmethyl ketone with at least one dihalo-triorganophosphorane of the general formula I $$R_3PHal_2 \qquad (I),$$

in which the radicals R can be the same or different and denote a saturated or unsaturated aliphatic $C_1$–$C_{20}$ hydrocarbon radical, a phenyl or ($C_1$–$C_4$ alkyl)phenyl radical, which may be optionally substituted by one or two fluorine, chlorine and/or nitro groups, P stands for phosphorus and Hal denotes chlorine, bromine, or iodine, at a temperature of from 80° to 130° C., where the dihalo-triorganophosphorane of the general formula (I) is synthesized in situ from triorganophosphane oxide or triorganophosphane sulfide of the general formula II $$R_3PA \qquad (II),$$

in which R is as defined above with respect to formula I and A stands for oxygen or sulfur, using a halogenating agent, wherein the triorganophosphane oxide or triorganophosphane sulfide is used in catalytic amounts.

2. A process as defined in claim 1, wherein a dichloro-triorganophosphorane of formula (I) is synthesized in situ by the reaction of a triorganophosphane oxide or triorganophosphane sulfide of formula (II) with phosgene.

3. A process as defined in claim 1, wherein a dichloro-tri($C_6$–$C_8$ alkyl)phosphorane, dichloro-triphenylphosphorane, dichloro-tri(4-chlorophenyl)phosphorane, dichloro-tri(4-fluorophenyl)phosphorane, dichloro-tri(4-nitrophenyl)phosphorane, or a mixture thereof is used.

4. A process as defined in claim 1, wherein cyclopropylmethyl ketone is halogenated in the absence of a solvent.

5. A process for the production of cyclopropylacetylene, wherein cyclopropylmethyl ketone is halogenated according to claim 1, and the halogenation product is treated with a strong base at a temperature of from −33° C. to 250° C.

6. A process as defined in claim 5, wherein the strong base used is potassium hydroxide or potassium methoxide in a glycol ether.

* * * * *

UNITED STATES PATENT AND TRADEMARK OFFICE
CERTIFICATE OF CORRECTION

PATENT NO.    : 6,207,864 B1
DATED         : March 27, 2001
INVENTOR(S)   : Henningsen et al.

Page 1 of 1

It is certified that error appears in the above-identified patent and that said Letters Patent is hereby corrected as shown below:

<u>Title page,</u>
Item [22], "Feb. 18, 1998" should be -- Feb. 17, 1998 --.
ABSTRACT, line 11, "800°" should be -- 80° --.

Signed and Sealed this

Fourteenth Day of May, 2002

Attest:

Attesting Officer

JAMES E. ROGAN
*Director of the United States Patent and Trademark Office*